United States Patent
Banerjee et al.

(10) Patent No.: US 11,083,416 B2
(45) Date of Patent: Aug. 10, 2021

(54) METHOD AND SYSTEM FOR DETECTION OF CORONARY ARTERY DISEASE IN A PERSON USING A FUSION APPROACH

(71) Applicant: Tata Consultancy Services Limited, Mumbai (IN)

(72) Inventors: Rohan Banerjee, Kolkata (IN); Anirban Dutta Choudhury, Kolkata (IN); Arpan Pal, Kolkata (IN); Parijat Dilip Deshpande, Pune (IN); Kayapanda Muthana Mandana, Kolkata (IN); Ramu Reddy Vempada, Bangalore (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 331 days.

(21) Appl. No.: 15/895,353

(22) Filed: Feb. 13, 2018

(65) Prior Publication Data
US 2018/0228444 A1   Aug. 16, 2018

(30) Foreign Application Priority Data
Feb. 16, 2017   (IN) .............................. 201721005479

(51) Int. Cl.
| | |
|---|---|
| *A61B 5/00* | (2006.01) |
| *A61B 5/024* | (2006.01) |
| *A61B 7/04* | (2006.01) |
| *G16H 50/20* | (2018.01) |
| *A61B 5/0533* | (2021.01) |

(Continued)

(52) U.S. Cl.
CPC .......... *A61B 5/7267* (2013.01); *A61B 5/0205* (2013.01); *A61B 5/02405* (2013.01); *A61B 5/02416* (2013.01); *A61B 5/0533* (2013.01); *A61B 5/318* (2021.01); *A61B 5/349* (2021.01); *A61B 5/7203* (2013.01); *A61B 7/04* (2013.01); *G06N 7/005* (2013.01); *G06N 20/00* (2019.01); *G16H 50/20* (2018.01)

(58) Field of Classification Search
CPC ....... A61B 5/02; A61B 5/024; A61B 5/02405; A61B 5/7203; A61B 5/7267
See application file for complete search history.

(56) References Cited

U.S. PATENT DOCUMENTS

| | | | | |
|---|---|---|---|---|
| 2011/0172505 | A1* | 7/2011 | Kim ................... | A61B 5/02007 600/301 |
| 2014/0171812 | A1* | 6/2014 | Johnson ............... | A61B 5/6833 600/485 |

(Continued)

*Primary Examiner* — Puya Agahi
(74) *Attorney, Agent, or Firm* — Finnegan, Henderson, Farabow, Garrett & Dunner, LLP

(57) ABSTRACT

A method and system for detection of coronary artery disease (CAD) in a person using a fusion approach has been described. The invention the detection of CAD in the person by capturing of a plurality of physiological signals such as phonocardiogram (PCG), photoplethysmograph (PPG), ECG, galvanic skin response (GSR) etc. from the person. A plurality of features are extracted from the physiological signals. The person is then classified as CAD or normal using the each of the features independently. The classification is done based on supervised machine learning technique. The output of the classification is then fused and used for the detection of the CAD in the person using a predefined criteria.

13 Claims, 6 Drawing Sheets

(51) Int. Cl.
*G06N 7/00* (2006.01)
*G06N 20/00* (2019.01)
*A61B 5/0205* (2006.01)
*A61B 5/318* (2021.01)
*A61B 5/349* (2021.01)

(56) References Cited

U.S. PATENT DOCUMENTS

| | | | |
|---|---|---|---|
| 2014/0316292 A1* | 10/2014 | McRae | A61B 5/0295 600/504 |
| 2015/0065847 A1* | 3/2015 | Choi | A61B 5/7275 600/407 |
| 2015/0157273 A1 | 6/2015 | An et al. | |
| 2016/0066859 A1 | 3/2016 | Crawford et al. | |

\* cited by examiner

METHOD AND SYSTEM FOR DETECTION OF CORONARY ARTERY DISEASE IN A PERSON USING A FUSION APPROACH

PRIORITY CLAIM

This U.S. patent application claims priority under 35 U.S.C. § 119 to: India Application No. 201721005479, filed on Feb. 16, 2016. The entire contents of the aforementioned application are incorporated herein by reference.

TECHNICAL FIELD

The present application generally relates to the field of coronary artery disease (CAD) detection. More particularly, but not specifically, the invention provides a non-invasive system and method for detection of coronary artery disease (CAD) using a fusion approach.

BACKGROUND

Coronary Artery Disease (CAD) is a common heart disease and one of the leading cause of death of an individual. CAD is formed due to deposition of cholesterol and other fatty materials over time on the inner walls of coronary arteries, thus restricting the normal blood flow, causing chest pain and heart attack. In spite of numerous works, an early non-invasive detection of CAD is an open research area till date.

Researchers found that certain non-invasive biomedical markers can identify CAD. The most commonly used marker for the same is Heart Rate Variability (HRV). HRV of a CAD patient is generally much lower compared to a normal subject. However, the gold standard technique for measuring HRV for a long duration, from the successive RR intervals of ECG signal is largely obtrusive and often impractical. Analysis of heart sound signal or phonocardiogram (PCG) can also be found in literature, as an alternative approach. Research reveals that, the spectral energy of diastolic heart sound above 130 Hz is higher for a CAD patient compared to a non CAD subject. However, PCG signal is extremely vulnerable to ambient noise and thus an accurate segregation of diastolic heart sound may not always be trivial. Moreover, many people have a faint heart sound, making them further difficult to process. Hence, accurate estimation of CAD from a single physiological signal is still an unsolved problem.

On the other hand, photoplethysmogram (PPG) is a simple low cost non-invasive technique that measures the instantaneous blood flow in capillaries. Time, frequency and morphological features of PPG are widely used to estimate several physiological parameters including heart rate, blood pressure, HRV etc. with commending accuracy. For the ease of deployment, PPG signal is used for extracting HRV related features instead of ECG. It is to be noted that, HRV related features can also be derived from PCG. However, this requires, acquisition of heart sound for a prolonged duration using a digital stethoscope, which is uncomfortable for a user. In addition to that, these techniques are expansive.

None of the prior art is directly and exactly related to coronary artery disease (CAD) detection from a physiological signal. They either broadly talk about the possible diagnosis of cardio-vascular diseases from such signals or are focused on the diagnosis of peripheral arterial disease (PAD). None of the prior art have talked about the fusion of different decisions for CAD diagnosis. Thereby, identifying coronary artery disease (CAD) patients by fusing the decisions of multiple classifier systems based on multiple physiological signals is still considered to be one of the biggest challenges of the technical domain.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for detection of coronary artery disease (CAD) in a person. The system comprises a plurality of physiological sensors, a memory and a processor in communication with the memory. The plurality of physiological sensors capture a plurality of physiological signals from the person. The processor further comprises a signal processing module, a feature extraction module, a classification module, a fusion module and a detection module. The signal processing module processes the plurality of physiological signals to remove a plurality of noises. The feature extraction module extracts time domain features, frequency domain features, time-frequency domain features and statistical features from each of the processed physiological signals. The classification module classifies the person from each of the features independently as CAD or normal using physiological signal classifiers, wherein the classification is done using a supervised machine learning technique. The fusion module fuses the output of the physiological signal classifiers. The detection module for detecting the presence of the coronary artery disease in the person using the physiological signal classifiers based on a predefined criteria.

In another embodiment, provides a non-invasive method for detection of coronary artery disease (CAD) in a person. Initially a plurality of physiological signals from the person is captured using a plurality of physiological sensors. At the next step, the plurality of physiological signals are processed to remove a plurality of noises using a signal processing module. Further, the time domain features, frequency domain features, time-frequency domain features and statistical features are extracted from each of the processed physiological signals using a feature extraction module. In the next step, the person from each of the features is classified independently using physiological signal classifiers as CAD or normal, wherein the classification is done using a supervised machine learning technique. The output of the physiological signal classifiers is then fused. And finally, the presence of coronary artery disease in the person is detected using the fused output of the physiological signal classifiers based on a predefined criteria.

In yet another embodiment, provides one or more non-transitory machine readable information storage mediums comprising one or more instructions, which when executed by one or more hardware processors perform actions including capturing a plurality of physiological signals from the person using a plurality of physiological sensors. Further, processing the plurality of physiological signals to remove a plurality of noises using a signal processing module. Then, extracting time domain features, frequency domain features, time-frequency domain features and statistical features from each of the processed physiological signals using a feature extraction module. Further, classifying the person from each of the features independently using physiological signal classifiers as CAD or normal, wherein the classification is done using a supervised machine learning technique. Furthermore, fusing the output of the physiological signal classifiers and then detecting the presence of coronary artery disease in the person using the fused output of the physiological signal classifiers based on a predefined criteria.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The words "comprising," "having," "containing," and "including," and other forms thereof, are intended to be equivalent in meaning and be open ended in that an item or items following any one of these words is not meant to be an exhaustive listing of such item or items, or meant to be limited to only the listed item or items.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present disclosure, the preferred, systems and methods are now described.

Some embodiments of this disclosure, illustrating all its features, will now be discussed in detail. The disclosed embodiments are merely exemplary of the disclosure, which may be embodied in various forms.

Before setting forth the detailed explanation, it is noted that all of the discussion below, regardless of the particular implementation being described, is exemplary in nature, rather than limiting.

Figure 1:
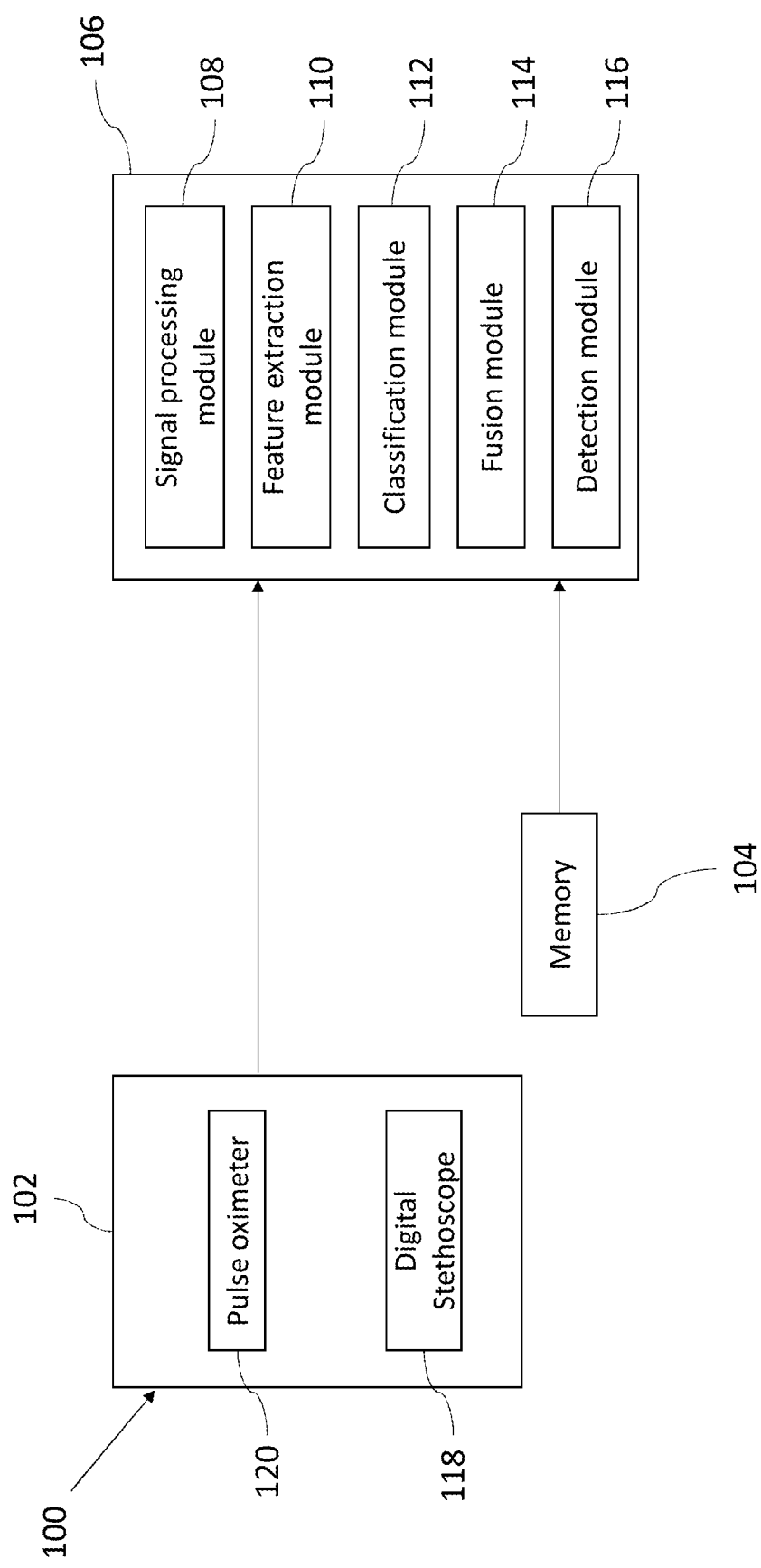
FIG. 1 illustrates a block diagram of a system for detection of coronary artery disease (CAD) in a person, in accordance with an embodiment of the disclosure.

Referring now to the drawings, and more particularly to FIG. 1, where similar reference characters denote corresponding features consistently throughout the figures, there are shown preferred embodiments and these embodiments are described in the context of the following exemplary system and/or method.

According to an embodiment of the disclosure, a system 100 for detection of coronary artery disease (CAD) in a person is shown in FIG. 1. The present disclosure provides a supervised learning approach for classifying the person as CAD/non CAD based on analysis of multiple low cost noninvasive physiological signals such as photoplethysmogram (PPG), electrocardiogram (ECG), phonocardiogram (PCG), galvanic skin rate (GSR), infrared videos etc. The disclosure provides a method through which physiological signals are captured non-invasively using low cost sensors. The disclosure also provides a sensor-agnostic system, i.e the method is independent to the quality of the sensors for capturing the physiological signals.

According to an embodiment of the disclosure, a block diagram of the system 100 is shown in FIG. 1. The system 100 includes a plurality of physiological sensors 102, a memory 104, and a processor 106 in communication with the memory 104. The memory 104 is configured to store a plurality of algorithms. The processor 106 further includes a plurality of modules for performing various functions. The plurality of modules access the plurality of algorithms stored in the memory 104 to perform various functions. The plurality of modules comprise a signal processing module 108, a feature extraction module 110, a classification module 112, a fusion module 114 and a detection module 116.

According to an embodiment of the disclosure, the system 100 includes the plurality of physiological sensors 112 for capturing the physiological signal from the person. In the present example, the system 100 is using phonocardiogram (PCG) signal and photoplethysmograph (PPG) signal for the detection CAD in the person. The use of other physiological signals such as galvanic skin response (GSR), electrocardiogram (ECG) etc. is well within the scope of this disclosure.

According to an embodiment of the disclosure, the system 100 is using a digital stethoscope 118 for collection of the heart sounds from the person. This is the low cost digital stethoscope 118, comprising an acoustically designed 3D printed cavity that can be attached to a smart phone for digitalizing and storing heart sounds. PCG is captured from each subject for a minute at a sampling rate of 8000 Hz in an uncontrolled environment of the catheterization laboratory (cath lab) of the hospital. This was done purposefully to make the system robust enough to deal with the background noise. Subsequently, PPG signal was collected from the right hand index finger of the subject using a fingertip pulse oximeter 120 at 60 Hz. The duration of PPG data collection was fixed for five minutes so that information regarding HRV can be preserved in the measurement. The PPG signal can also be collected from any other peripheral part of the body such as ear, toe and forehead.

According to an embodiment of the disclosure, the system 100 also includes the signal processing module 108. The signal processing module 108 is configured to remove a plurality of noises from the captured PCG signal and the PPG signal. The captured PCG signal is extremely vulnerable to ambient noise in audible range. Even in a constrained quiet environment, the frictional noise generated at the contact region of human body and stethoscope corrupts the signal heavily. Segregation of fundamental heart sounds from a noisy PCG is a tricky task. A logistic regression based HSMM is applied for segregating heart sounds on one very clean signal and one partially noisy signal from the input data. Thus, instead of segregating the fundamental heart sounds, a window based approach was used.

The relevant information regarding heart sound is typically stored well below 500 Hz. A low pass filter is used to remove all the frequency components above 500 Hz. Subsequently, the signal is broken into small overlapping windows to retain the temporal information corresponding to individual heartbeat. Since the heart rate of a stable cardiac patient does not go below 30 bpm, a window length of 2 seconds duration ensures the presence of at least one complete heart beat in every window. Time and frequency domain features are extracted from each window.

Table I indicates that CAD patients typically possess a higher value of spectral power ratio but reduced spectral centroid, roll-off, flux and time domain kurtosis values compared to a non CAD subject. For extracting frequency domain features, the Short Time Fourier Transform (STFT) of each window is computed to get the spectrum. In Table I, for $k^{th}$ time window $W_k(t)$, it was assumed N and $S_k(w)$ to be the length of the window and the corresponding spectral power amplitude respectively for representing the features.

TABLE 1

Ranges of PCG Features in the Dataset

| No. | Feature name | CAD Range mean ± std | Non CAD Range mean ± std |
|---|---|---|---|
| 1 | Mean spectral power ratio between 0-100 Hz and 100-150 Hz | 0.041 ± 0.017 | 0.031 ± 0.012 |
| 2 | Mean spectral centroid $(\Sigma_{\omega=1}^{N} \omega * S_k(\omega)/\Sigma_{\omega=1}^{N} \omega)$ | 563 ± 60 | 589 ± 88 |
| 3 | Mean spectral roll-off $(0.85 * \Sigma_{\omega=1}^{N} S_k(\omega))$ | 2486 ± 1660 | 2882 ± 1512 |
| 4 | Mean spectral flux $(||S_k(\omega) - S_{k-1}(\omega)||)$ | 98.21 ± 55.28 | 113.22 ± 49.82 |
| 5 | Mean kurtosis of all time window | 18.53 ± 5 | 30.79 ± 13.95 |

Figure 2:
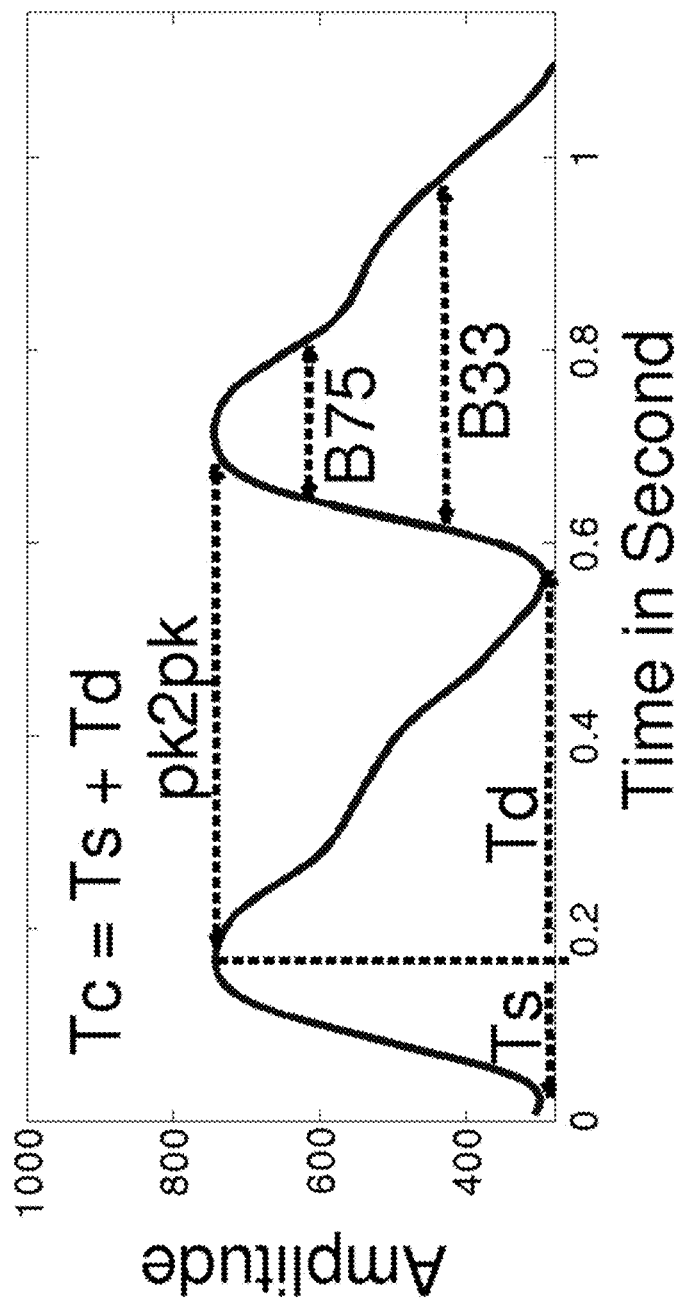
FIG. 2 shows a sample PPG signal captured from a person, in accordance with an embodiment of the present disclosure.

Further, the PPG signal also contains several noise components. The low frequency noise present in it is caused due to the respiratory rate of the subject (typically 14-18 times/minute). Several high frequency noise components are also present due to motion artifacts and circuit noise of the sensor. To mitigate those, captured PPG signal is fed into a band pass filter having cut-off frequencies of 0.5 Hz and 10 Hz. FIG. 2 shows 2 complete cycles of a sample PPG signal, indicating some of its features. Table II details different features used in this disclosure along with their ranges for CAD and non CAD subjects. Out of these, feature 1, 2, 3, 5, 7, 9 and 11 are related to HRV and the rest are related to pulse shape.

TABLE II

Ranges of PPG Features in the dataset

| No. | Feature name | CAD Range mean ± std | Non CAD Range mean ± std |
|---|---|---|---|
| 1 | Spectral power of NN interval in 0-0.04 Hz | 1.32 ± 0.010 | 0.99 ± 0.002 |
| 2 | Spectral power of NN interval in 0.04-0.15 Hz | 0.08 ± 0.050 | 0.02 ± 0.005 |
| 3 | Spectral power of NN interval in 0.15-0.4 Hz | 0.008 ± 0.001 | 0.006 ± 0.001 |
| 4 | Mean of pulse duration $(T_c)$ sec. | 0.77 ± 0.14 | 0.85 ± 0.14 |
| 5 | Std of pulse duration $(T_c)$ | 0.07 ± 0.05 | 0.09 ± 0.05 |
| 6 | Mean of relative crest time $(T_s/T_c)$ | 0.29 ± 0.03 | 0.27 ± 0.03 |
| 7 | Std of relative crest time $(T_s/T_c)$ | 0.02 ± 0.01 | 0.03 ± 0.01 |
| 8 | Mean of relative diastolic time $(T_d/T_c)$ | 0.71 ± 0.04 | 0.73 ± 0.03 |
| 9 | std of relative diastolic time $(T_d/T_c)$ | 0.03 ± 0.01 | 0.04 ± 0.02 |
| 10 | Mean of time ratio $(T_d/T_s)$ | 2.49 ± 0.49 | 2.81 ± 0.53 |
| 11 | std of of time radio time $(T_d/T_s)$ | 0.35 ± 0.25 | 0.43 ± 0.19 |

According to an embodiment of the disclosure, the processed PCG signal and the processed PPG signal are further provided as input to the feature extraction module 110. The feature extraction module 110 extracts time domain features, frequency domain features, time-frequency domain features and statistical features from each of the processed physiological signals. The list of various features is provided in table II. It should be appreciated that many other features can also be extracted from the plurality of physiological signals. The features are a set of combination of features corresponding heart beat morphology and heart rate variability (HRV) of the person. The features corresponding to the heart beat morphology and heart valve functioning are extracted using wide band PCG signal. While, the features corresponding to the detailed heart rate variability are extracted using narrow band PPG signal and ECG signal.

According to an embodiment of the disclosure, the system 100 includes the classification module 112. The classification module 112 is configured to classify the person from each of the features independently using physiological signal classifiers. In the present example the physiological signal classifiers comprise a PPG classifier and a PCG classifier. A machine learning method has been used for the classification. In an embodiment support vector machine (SVM) is used for classification. Both linear and non-linear SVMs were explored and it is found that, non-linear SVM with a Radial Basis Function (RBF) kernel produces the optimum performance. Though the use of any other supervised learning techniques such as artificial neural network (ANN) and random forest etc. is well within the scope of this disclosure.

According to an embodiment of the disclosure, the system 100 further comprises the fusion module 114 and the detection module 116. The fusion module 114 is configured to fuse the output of the PPG classifier and the PCG classifier. The SVM separates two classes in a multidimensional feature space by fitting an optimal separating hyper-plane to the training samples. The objective function of SVM aims to maximize the margin between the hyper-plane and the closest training samples (support vectors). For a given sample, higher the distance to the hyper-plane, the more reliable the output class label is. This fundamental concept of SVM is used in the present disclosure for fusing the outcomes of two independent classifiers.

The detection module 116 configured to detect the person if he is a CAD or non-CAD person. For the person if there is a classification mismatch between PCG and PPG based classifiers, the classifier producing higher absolute distance of the test data-point form its separating hyper-plane is considered as the reliable source for the final decision making. Thus, for n number of independent classifiers, if the outcome of a classifier is marked as +1 for CAD and −1 for non CAD, then for each subject, final value F is computed as follows:

$$F = \sum_{i=1}^{n} pred_i * dist_i$$

Here for $i^{th}$ classifier (n=2, i.e. PCG and PPG), $pred_i$ and $dist_i$ are the predicted label and the absolute distance value of the data point from SVM hyper-plane. A positive value of F indicates the final predicted label as CAD after fusion and non CAD otherwise.

Figure 3A:
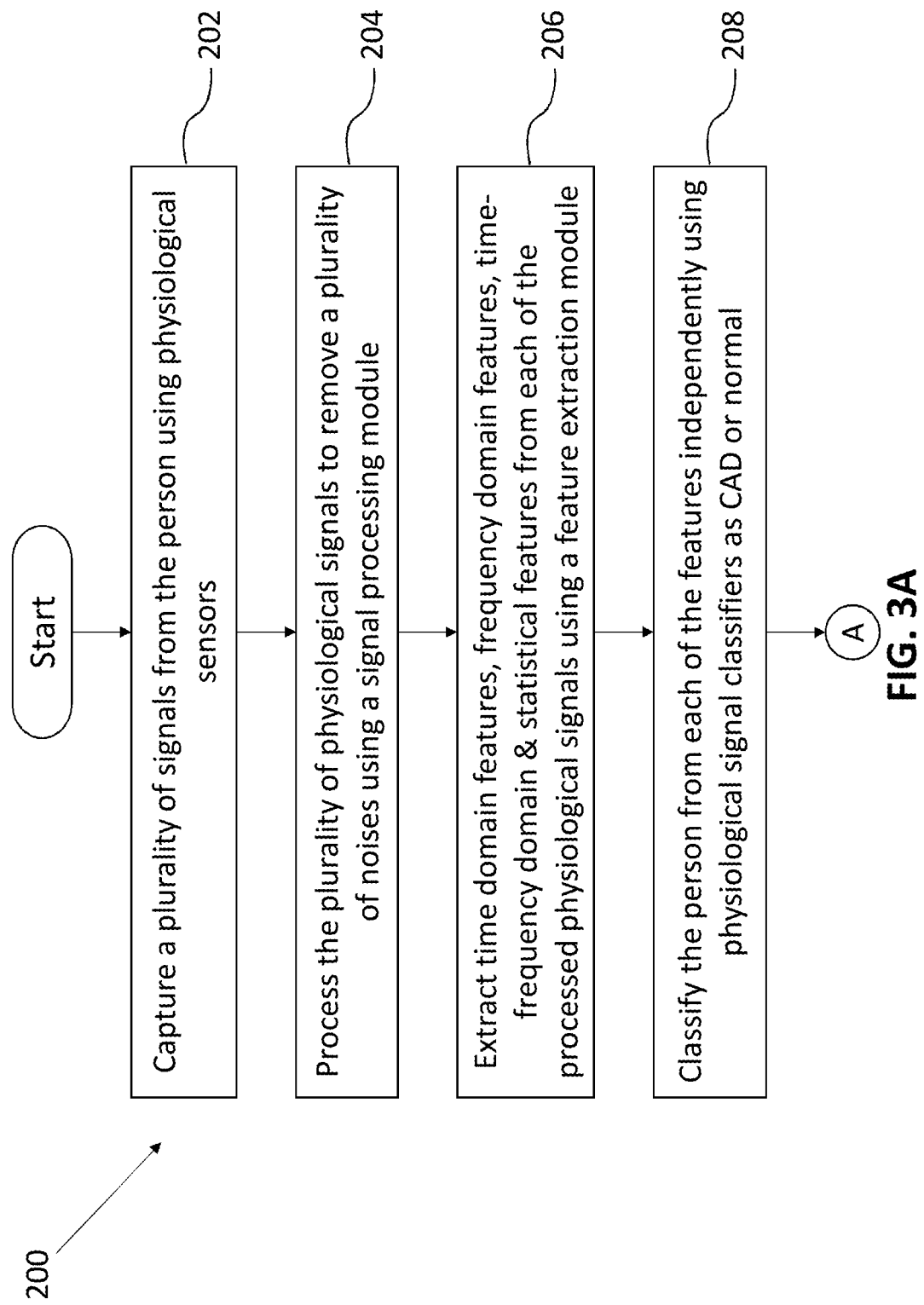
FIGS. 3A and 3B is a flowchart illustrating the steps involved for detection of coronary artery disease (CAD) in a person, in accordance with an embodiment of the disclosure
Figure 3B:
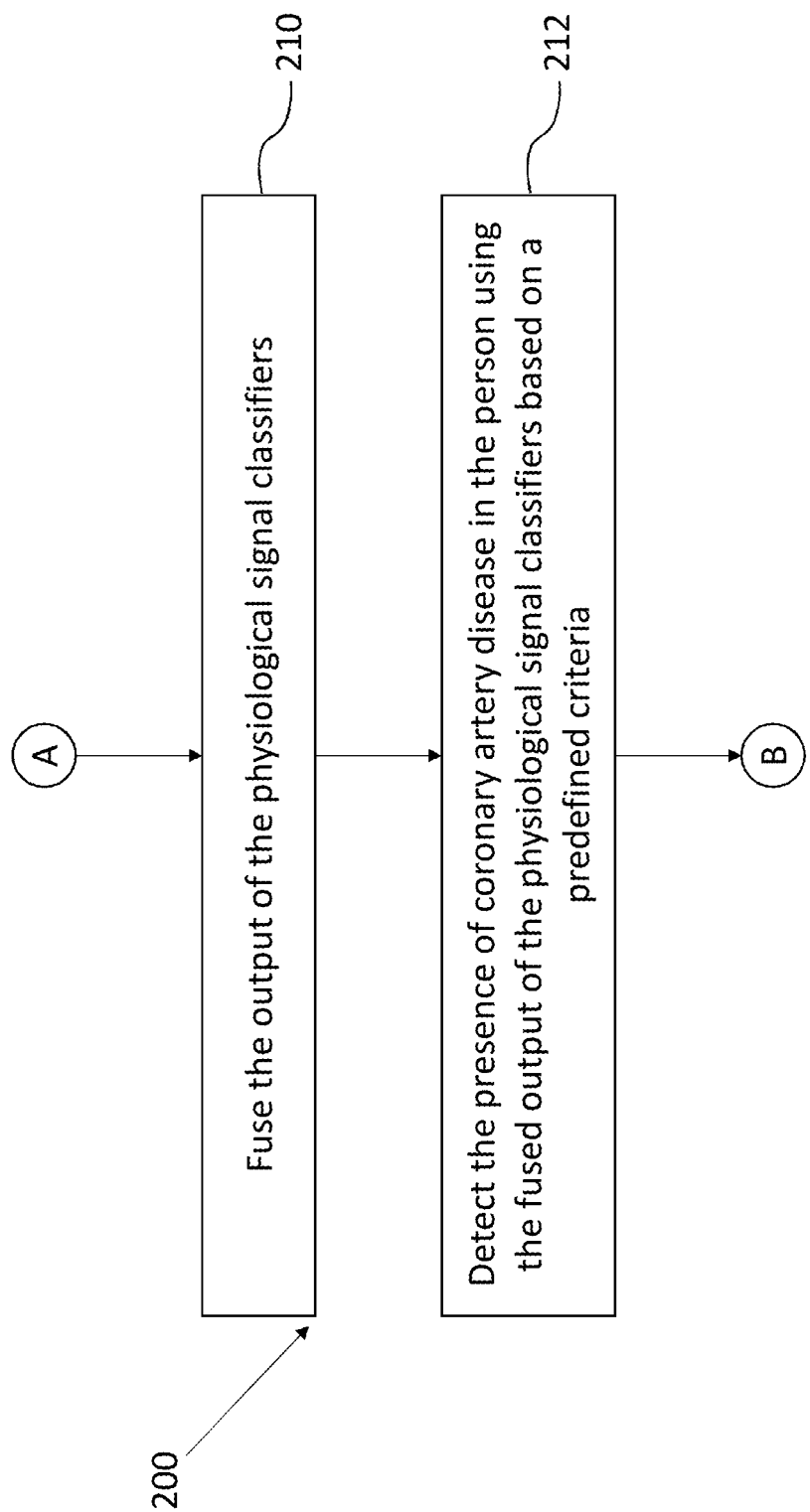

In operation, a flowchart 200 for detection of coronary artery disease (CAD) in a person is shown in FIG. 3A-3B. Initially at step 202, the plurality of physiological signals are captured from the person using the plurality of physiological sensors 102. In the present example, the PCG signal and PPG signal are used for the classification. In the next step 204, the plurality of physiological signals are processed to remove a plurality of noises using the signal processing module 108.

At step 206, time domain features, frequency domain features, time-frequency domain features and statistical features are extracted from each of the processed physiological signals using the feature extraction module 110. In the next step 208, the person is classified from each of the features independently using physiological signal classifiers as CAD or normal. The classification is done using a supervised machine learning technique. In an embodiment support vector machine has been used for the classification.

At step 210, the output of the physiological signal classifiers are fused using the fusion module 114. And finally, the presence of coronary artery disease is detected in the person using the fused output of the physiological signal classifiers based on a predefined criteria. The predefined criteria comprises if there is a classification mismatch between the outputs of the physiological signal classifiers, the reliable classifier is chosen based on the outcome of the classifier which has the highest probability score out of the each of the physiological signal classifiers.

According to an embodiment of the disclosure, the method for detection of coronary artery disease in the person can be validated with the help of following experimental findings. The experiments were performed on the twenty six participants The experimental dataset includes CAD patient with ranging percentages of heart blockage while non CAD population consists of both healthy subjects as well as non-cardiac patients. Initially, 11 healthy subjects aged between 22-25 years with no prior history of cardiovascular diseases were selected as non CAD subjects. 4 patients, aged between 45-68 years, being treated in an urban hospital in Kolkata, India for non-cardiovascular diseases, were also included in the dataset. Finally, 10 angiography-proven CAD patients, aged between 38-82 years were selected from the same hospital. Thus the corpus had grown into a total of 25 subjects, including 15 non CAD and 10 CAD subjects. Out of 10 CAD patients, 2 patients had a marginal heart blockage of 30% while the rest had a blockage of 80%. All the subjects were told about the purpose of experiments and the entire dataset was preserved anonymously.

The in-house digital stethoscope for collection of heart sounds. This is a low cost digital stethoscope, comprising an acoustically designed 3D printed cavity that can be attached to a smart phone for digitalizing and storing heart sounds. PCG is captured from each subject for a minute at a sampling rate of 8000 Hz in an uncontrolled environment of the catheterization laboratory (cath lab) of the hospital. This was done purposefully to make our system robust enough to deal with the background noise. Subsequently, PPG signal was collected from the right hand index finger of the subject using a fingertip pulse oximeter at 60 Hz. The duration of PPG data collection was fixed for five minutes so that information regarding HRV can be preserved in the measurement.

For an exhaustive validation on a relatively smaller dataset, Leave One Out Cross Validation (LOOCV) approach was used for reporting the results. Performance analysis was done in terms of sensitivity (Se) and specificity (Sp) of identifying CAD patients and overall accuracy is measured as Acc=(Se+Sp)=2.

Figure 4:
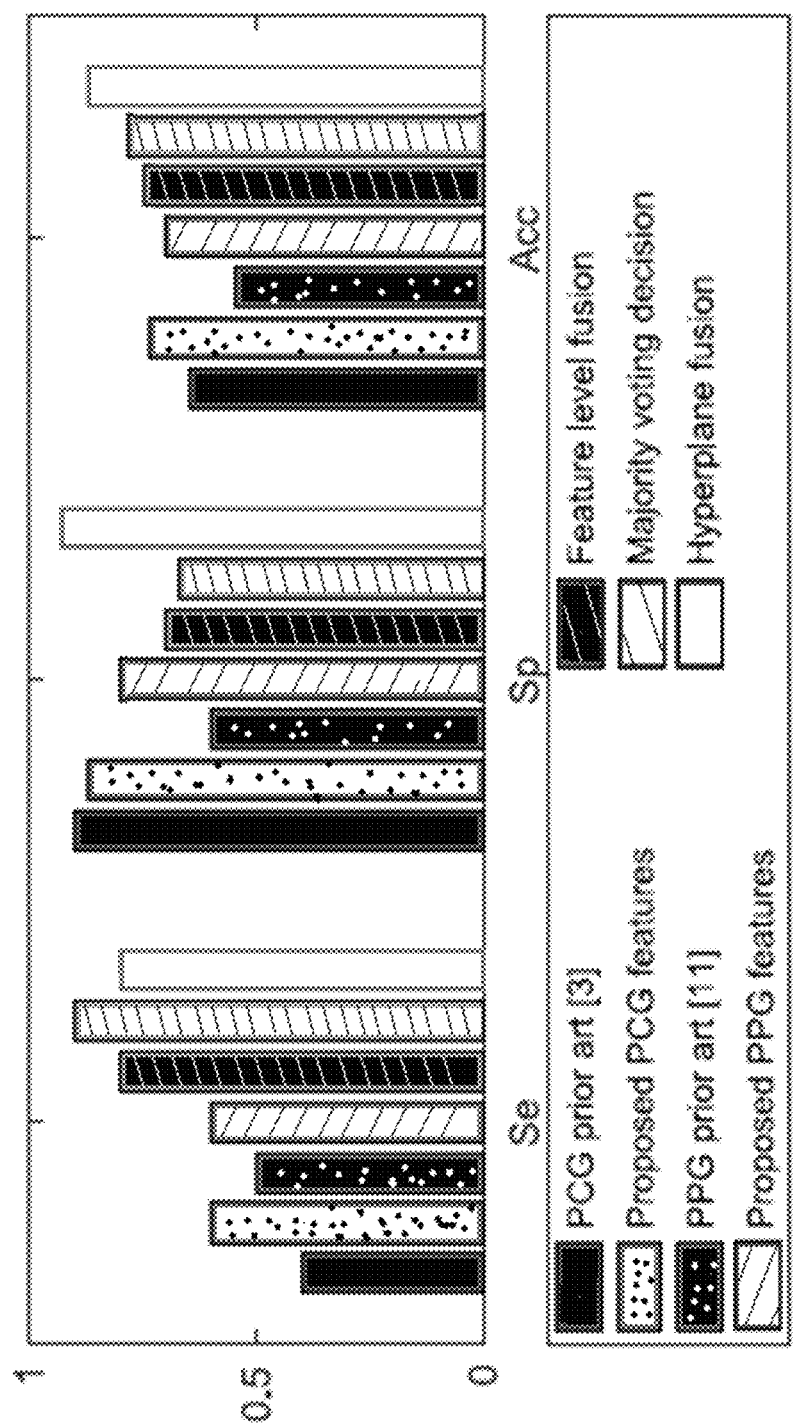
FIG. 4 shows the graphical representation of comparative analysis between different classifiers, in accordance with an embodiment of the disclosure.

FIG. 4 shows a comparative analysis among different methodologies explored in this paper along with certain popular prior art techniques. Prior art models the diastolic portion of PCG using an autoregressive (AR) model for identifying CAD, whereas prior art is a PPG based approach that considers relative crest time as the discriminative feature. It can be observed that our proposed PCG and PPG features outperform prior art. However, the sensitivity scores obtained by either of them is largely unsatisfactory (0:6). A simple feature level fusion was also performed, where all 16 features (5 PCG features+11 PPG features) are combined to form a composite feature set for classification. It is observed that in spite of an improvement in sensitivity (0:8), the specificity (0:7) falls, resulting in a similar overall accuracy score to the earlier methodologies. Subsequently, a simple majority voting based fusion was applied at decision level as a benchmark approach. Here a subject is declared as CAD, if either of the classifiers marks him/her as CAD. Although a very high sensitivity (0:9) is achieved in this approach, the specificity drops significantly (0:67), resulting in a minimum improvement in overall accuracy (0:79).

Figure 5A:
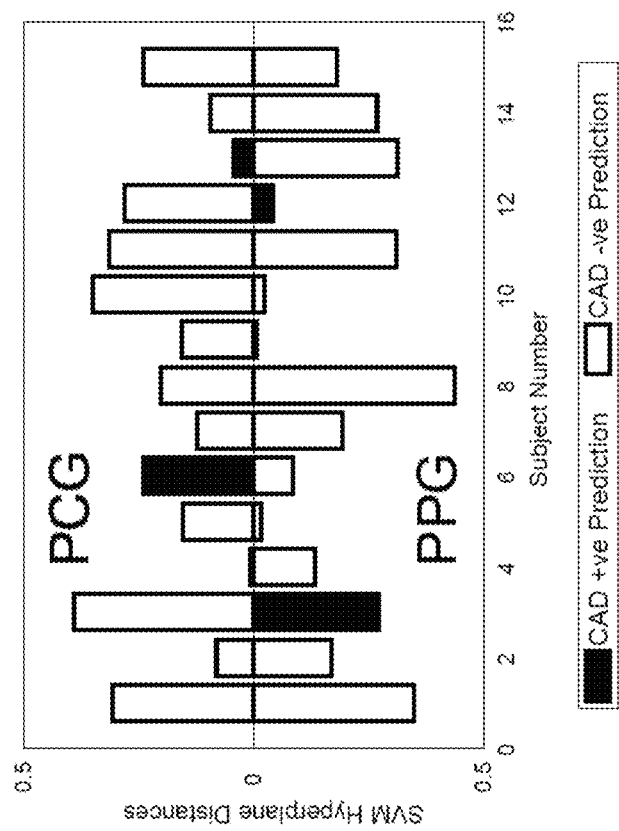
FIGS. 5A and 5B shows the graphical representation of subject level analysis of hyper-plane based fusion, in accordance with an embodiment of the disclosure.
Figure 5B:
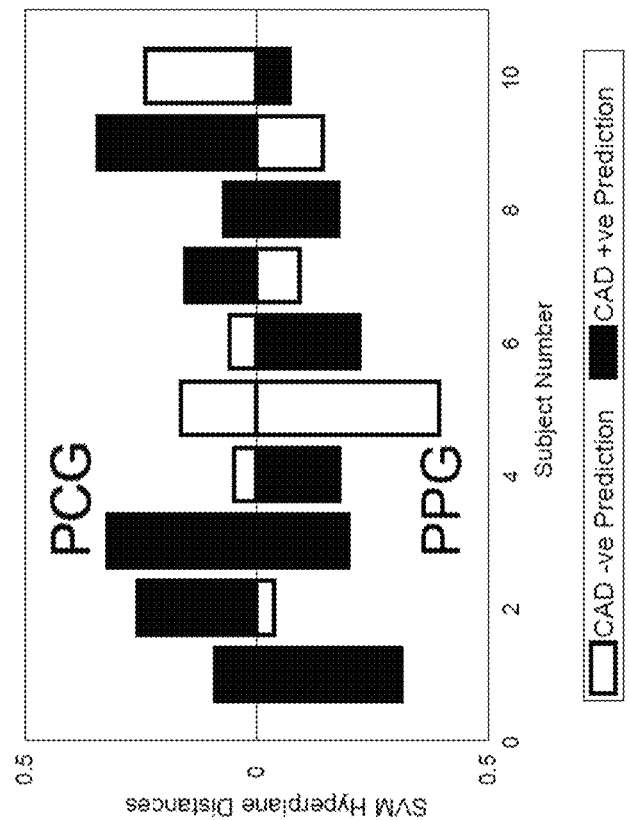

A significant improvement in both sensitivity (0:8) and specificity (0:93) can be simultaneously achieved by incorporating the proposed hyper-plane based fusion approach, resulting in the maximum accuracy (Acc=0:87) among all. FIGS. 5A and 5B provides a detailed outcome of the fusion technique for all subjects. Here, it was shown that the predicted labels by both the classifiers along with the absolute distance values from the SVM hyper-plane to show the effect of fusion.

As shown in FIG. 5A, out of 10 CAD subjects, there is a mismatch between PPG and PCG classifiers in 6 cases. In 5 out of 6 such cases (except Subject 10), the proposed fusion technique yields the correct decision. However, in non CAD subjects, 5 out of 15 cases (Subject 3, 6, 9, 12 and 13 of FIG. 5B) had this mismatch of decisions and the proposed fusion technique was able to correctly resolve 4 out of those 5 conflicts. A closer inspection further revealed that one of the two borderline CAD patients having 30% blockage (Subject 5 of FIG. 5A) was missed by both PPG and PCG classifiers. A possible reason is that PPG and PCG features of those subjects are similar to a normal person rather than a severe CAD patients, hence they are very difficult to identify even by the doctors. The only false detected non CAD subject (Subject 6 of FIG. 5B) was a patient being treated for asthma related issues. In spite of being detected correctly by the PPG classifier, the fusion algorithm fails to identify the subject due to the strong confidence score provided by the PCG classifier as CAD. It remains to be seen whether, PCG features of an asthma patient contains any similarity of a CAD patient.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example. The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

We claim:

1. A non-invasive method for detection of coronary artery disease (CAD) in a person, the method comprising a processor implemented steps of:
    capturing a plurality of physiological signals from the person using a plurality of physiological sensors, wherein the plurality of physiological signals includes at least one of phonocardiogram (PCG) signal, photoplethysmogram (PPG) signal, and electrocardiogram (ECG) signal;
    processing the plurality of physiological signals to remove a plurality of noises using a signal processing module;
    extracting features from each processed physiological signal of the plurality of physiological signals using a feature extraction module, wherein the features comprises at least one of time domain features, frequency domain features, time-frequency domain features and statistical features, wherein the features corresponding to heart beat morphology are extracted using a wide band PCG signal, and wherein the features corresponding to heart rate variability (HRV) are extracted using a narrow band PPG signal and the ECG signal;
    forming composite feature sets from a combination of extracted features corresponding to the heart beat morphology and the HRV;
    classifying the person for each of the composite feature sets independently using a plurality of physiological signal classifiers, as CAD or normal, wherein the classification is done using a supervised machine learning technique;
    fusing an output of each of the physiological signal classifiers by a hyper-plane based fusion approach, to produce a fused output; and
    detecting a presence of coronary artery disease in the person by choosing a particular physiological signal classifier to detect CAD, and wherein the particular physiological signal classifier is chosen based on the fused output.

2. The method of claim 1, wherein the predefined criteria comprises choosing classifier if there is a classification mismatch between the output of each of the physiological signal classifiers.

3. The method of claim 2, wherein the classifier is chosen based on an outcome of the classifier which has a highest accuracy out of the each of the physiological signal classifiers.

4. The method of claim 1, wherein the physiological signal classifiers include a PCG classifier, a PPG classifier and an ECG classifier.

5. The method of claim 1, wherein the PPG signal is extracted from the person's peripheral body parts.

6. The method as claimed in claim 5, wherein the person's peripheral body parts are at least one of fingertip, ear, toe or forehead.

7. The method of claim 1, wherein the ECG signal is captured from a portable single lead ECG machine and PCG is captured using a digital stethoscope.

8. The method as claimed in claim 1, wherein the classification of CAD patients and non-CAD patients is performed by using machine learning methods.

9. The method of claim 1, wherein the method is a sensor agnostic.

10. The method of claim 1, further comprising using a low pass filter for filtering the PCG signal with frequency above 500 Hz.

11. The method of claim 1, further comprising using a band pass filter for filtering the PPG signal with frequency between 0.5 Hz and 10 Hz.

12. A non-invasive system for detection of coronary artery disease (CAD) in a person, the system comprises:
   a plurality of physiological sensors for capturing a plurality of physiological signals from the person, wherein the plurality of physiological signals includes at least one of phonocardiogram (PCG) signal, photoplethysmogram (PPG) signal, and electrocardiogram (ECG) signal;
   a memory; and
   a processor in communication with the memory, the processor further comprises:
      a signal processing module processing the plurality of physiological signals to remove a plurality of noises;
      a feature extraction module for:
         extracting features from each processed physiological signal of the plurality of physiological signals, wherein the features comprises at least one of time domain features, frequency domain features, time-frequency domain features and statistical features, wherein the features corresponding to heart beat morphology are extracted using a wide band PCG signal, and wherein the features corresponding to heart rate variability (HRV) are extracted using a narrow band PPG signal and the ECG signal; and
         forming composite feature sets from a combination of extracted features corresponding to the heart beat morphology and the HRV;
      a classification module for classifying the person for each of the composite feature sets independently, as CAD or normal, using a plurality of physiological signal classifiers, wherein the classification is done using a supervised machine learning technique;
      a fusion module for fusing an output of each of the physiological signal classifiers by a hyper-plane based fusion approach, to produce a fused output; and
      a detection module for detecting a presence of the coronary artery disease in the person by choosing a particular physiological signal classifier to detect CAD, and wherein the particular physiological signal classifier is chosen based on the fused output.

13. One or more non-transitory machine readable information storage mediums comprising one or more instructions which when executed by one or more hardware processors perform actions comprising:
   capturing a plurality of physiological signals from the person using a plurality of physiological sensors, wherein the plurality of physiological signals includes at least one of phonocardiogram (PCG) signal, photoplethysmogram (PPG) signal, and electrocardiogram (ECG) signal;
   processing the plurality of physiological signals to remove a plurality of noises using a signal processing module;
   extracting features from each processed physiological signal of the plurality of physiological signals using a feature extraction module, wherein the features comprises at least one of time domain features, frequency domain features, time-frequency domain features and statistical features, wherein the features corresponding to heart beat morphology are extracted using a wide band PCG signal, and wherein the features corresponding to heart rate variability (HRV) are extracted using a narrow band PPG signal and the ECG signal;
   forming composite feature sets from a combination of extracted features corresponding to the heart beat morphology and the HRV;
   classifying the person for each of the composite sets features independently using a plurality of physiological signal classifiers, as CAD or normal, wherein the classification is done using a supervised machine learning technique;
   fusing an output of each of the physiological signal classifiers by a hyper-plane based fusion approach, to produce a fused output; and
   detecting a presence of coronary artery disease in the person by choosing a particular physiological signal classifier to detect CAD, and wherein the particular physiological signal classifier is chosen based on the fused output.

* * * * *